(12) United States Patent
Herrmann

(10) Patent No.: US 12,039,623 B2
(45) Date of Patent: Jul. 16, 2024

(54) REGISTRATION OF EMERGENCIES

(71) Applicant: Q2M2 APS, Virum (DK)

(72) Inventor: Ivan Tengbjerg Herrmann, Copenhagen (DK)

(73) Assignee: Q2M2 APS, Virum (DK)

( * ) Notice: Subject to any disclaimer, the term of this patent is extended or adjusted under 35 U.S.C. 154(b) by 52 days.

(21) Appl. No.: 17/605,368

(22) PCT Filed: Apr. 24, 2020

(86) PCT No.: PCT/EP2020/061462
§ 371 (c)(1),
(2) Date: Oct. 21, 2021

(87) PCT Pub. No.: WO2020/216900
PCT Pub. Date: Oct. 29, 2020

(65) Prior Publication Data
US 2022/0215497 A1 Jul. 7, 2022

(30) Foreign Application Priority Data
Apr. 26, 2019 (DK) .............. PA 2019 70265

(51) Int. Cl.
*G06Q 50/26* (2024.01)
(52) U.S. Cl.
CPC .................. *G06Q 50/265* (2013.01)
(58) Field of Classification Search
CPC .................................................. G06Q 50/265
See application file for complete search history.

(56) References Cited

U.S. PATENT DOCUMENTS

| | | | | |
|---|---|---|---|---|
| 6,089,943 | A * | 7/2000 | Lo ............ | A63H 3/28 446/72 |
| 9,286,440 | B1 | 3/2016 | Carter et al. | |
| 2012/0191476 | A1* | 7/2012 | Reid ............ | G16H 10/65 705/3 |
| 2014/0114691 | A1 | 4/2014 | Pearce | |
| 2014/0205155 | A1* | 7/2014 | Chung ............ | G06Q 50/26 382/115 |
| 2014/0239057 | A1* | 8/2014 | Galvin, Jr. ......... | H04W 4/02 235/375 |

(Continued)

FOREIGN PATENT DOCUMENTS

| | | |
|---|---|---|
| JP | 2009032225 | 2/2009 |
| JP | 2011034328 | 2/2011 |

*Primary Examiner* — Dennis W Ruhl
(74) *Attorney, Agent, or Firm* — DUANE MORRIS LLP; Gregory M. Lefkowitz; Joaquin Hernandez

(57) ABSTRACT

Disclosed is a system for registering emergency situations, the system comprises: a portable electronic device; an online server configured to communicate with the portable electronic device; and a first booklet. The online server is further configured to: in accordance with receiving the first primary identification parameter, registering an event in a server database of an occurrence of the primary emergency situation at a first location based on the first primary identification parameter, wherein the first location corresponds to a location of the first booklet, and in accordance with receiving the first secondary identification parameter, registering an event in the server database of an occurrence of the secondary emergency situation at the first location based on the first secondary identification parameter.

14 Claims, 1 Drawing Sheet

(56) References Cited

U.S. PATENT DOCUMENTS

| | | | |
|---|---|---|---|
| 2014/0339296 A1* | 11/2014 | McAdams | G06F 16/9554 |
| | | | 235/375 |
| 2015/0161350 A1* | 6/2015 | Chang | G16H 20/10 |
| | | | 235/494 |
| 2015/0227694 A1* | 8/2015 | Grimley | G16H 15/00 |
| | | | 705/3 |
| 2016/0335236 A1* | 11/2016 | Webster | G16H 40/67 |
| 2018/0075154 A1 | 4/2018 | Broselow | |

* cited by examiner

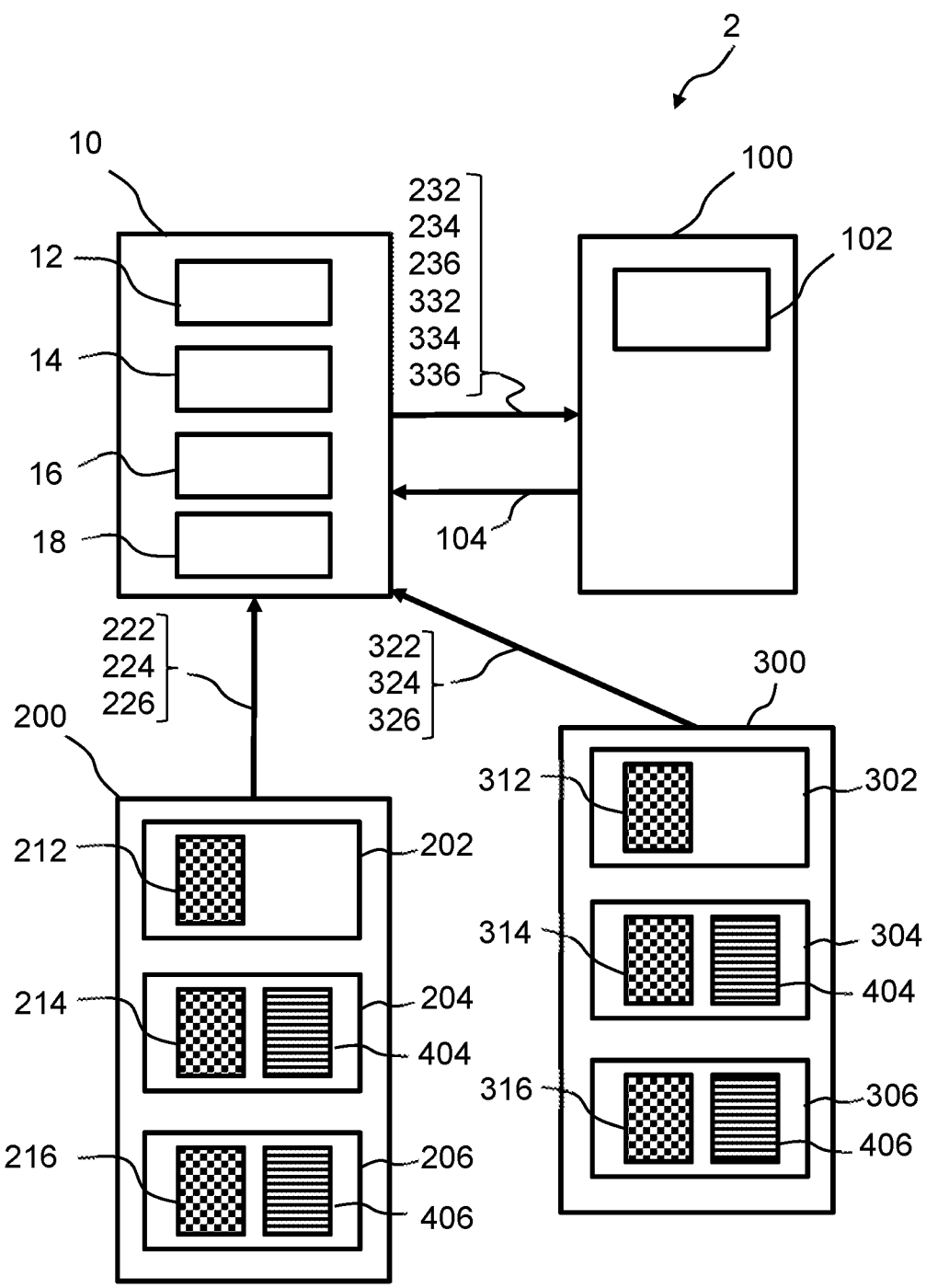

REGISTRATION OF EMERGENCIES

CROSS-REFERENCE TO RELATED APPLICATIONS

This application is a § 371 national stage entry of International Application No. PCT/EP2020/061462, filed Apr. 24, 2020, which claims priority to Danish Patent Application No. PA 2019 70265, filed Apr. 26, 2019, the entire contents of which are incorporated herein by reference.

The present disclosure relates to a system for registering emergency situations. In particular a system comprising a physical booklet comprising instructions for handling such emergency situations.

BACKGROUND

For first responders to an emergency, such as personal at a sports venue, lifeguards on a beach or at a public pool, or similar, it may be beneficial or even required by authorities that any emergency (or other critical situation in the following collectively labelled as an emergency) is registered. Such registration further makes it possible to do statistics on incidents in order to support risk analysis and development of "best practice" of responding to or being prepared for emergency situations, or optimally allow prevention or reduction of situations to occur.

Such registration of events may be provided using traditional paper forms where all inquiries are registered on paper. To allow later computational data process, the collected data must afterwards be entered into a computer manually. Alternatively, registration may be provided using electronic forms, e.g. placed on computers, tablets or smartphones, or on an online server. However, to fill out such form an operator needs an electronic device, such as a tablet, to fill a various number of pre-specified check boxes, scales, text boxes etc. In both cases a burden is put on the first responder, who needs to spend time and effort in completing and filing such forms.

Both of the two systems will typically require, at least, several minutes work for the registration of just one incident. However, for many types of registrations it is typically much more than just minutes that is required for registering just one incident. For example, registration of a broken arm, vomiting, head injury, or drowning incidents at a swimming pool can easily take more than 30 minutes per incident. Similar time consumption could be expected for registrations in sports clubs, e.g. football clubs, horse riding clubs etc. or institutions like kindergartens and schools.

Therefore, there is an increased risk that much registration is never done and hence never enters databases from where evidence-based risk analysis may be conducted.

Consequently, any risk analysis that is based on such unrepresentative data may lead to inefficient risk management. For example, if none or only a minor proportion of the vomiting incidents in swimming pools are registered it will lead to incorrect risk analysis and furthermore inefficient risk reduction control measures.

SUMMARY

It is an object of the present disclosure to provide a solution which copes with at least some of the disadvantages of the known solutions for registering emergency situations. Emergency situations may comprise personal injuries, hazards, critical situations, dangers or risk of dangers. Emergency situations may, for example, be a missing person, a person suffering cardiac arrest, a person suffering a concussion, damaged or unstable structures, etc.

Thus, the present disclosure relates to a system for registering emergency situations and elements thereof as disclosed in the appended claims.

It is an advantage of the disclosure, that a system is provided, which provides for quick, e.g. less than a minute, data collection of emergency situations. Thus, the present disclosure facilitates an enhanced data collection, which may be used for enhanced risk analysis and therefore also much more cost-efficient risk management.

BRIEF DESCRIPTION OF THE FIGURES

Embodiments of the disclosure will be described in more detail in the following with regard to the accompanying figures. The figures show one way of implementing the present invention and are not to be construed as being limiting to other possible embodiments falling within the scope of the attached claim set.

FIG. 1 is a schematic block diagram illustrating a system.

DETAILED DESCRIPTION

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 is a schematic block diagram illustrating a system 2 for registering emergency situations. The system 2 comprises a portable electronic device 10, an online server 100, a first booklet 200 and an optional second booklet 300. The system could further comprise additional booklets, such as a third booklet, a fourth booklet, etc.

The booklets 200, 300 may be produced on robust and waterproof materials, such as foamed PVC or plastic paper. The booklets 200, 300 may be produced in a portable and pocket size format.

The portable electronic device 10 may comprise a camera 12, a processing unit 14, memory 16 and/or a wireless transceiver 18. The portable electronic device 10 may be a smart phone or a tablet.

The online server 100 is configured to communicate with the portable electronic device 10. The portable electronic device 10 is configured to communicate with the online server 100. The communication between the online server 100 and the portable electronic device 10 could be done via wireless communication, such as WIFI or Bluetooth, or a combination of communication protocols. The communication between the online server 100 and the portable electronic device 10 may be provided over the internet. The communication between the online server 100 and the portable electronic device 10 may be effected through a plurality of servers.

The first booklet 200 comprises a plurality of pages, e.g. a plurality of first pages 202, 204, 206. The plurality of first pages includes a first primary page 204 and a first secondary page 206. The plurality of first pages may comprise a first main page 202. The first main page 202 may be a cover page of the first booklet 200.

The second booklet 300 comprises a plurality of pages, e.g. a plurality of second pages 302, 304, 306. The plurality of second pages includes a second primary page 304 and a second secondary page 306. The plurality of second pages may comprise a second main page 302. The second main page 302 may be a cover page of the second booklet 300.

At least some of the pages, such as at least some of the first pages and/or some of the second pages comprises instructions 404, 406 for handling of emergency situation, e.g. the known, to date, best possible handling for a particular emergency situation. For example, the instructions may be standard operating procedures for handling various emergency situations. For example one page may comprise instructions for handling an incident of nose bleeding, another page may comprise instructions for handling an incident of cardiac arrests, and yet another page may comprise instructions for handling damaged or dangerous structures, e.g. a broken railing. The instructions may comprise a primary instruction 404 and/or a secondary instruction 406. The instructions may comprise further instructions, e.g. including a tertiary instruction.

The first booklet 200 and the second booklet 300 may comprise the same instructions, e.g. the primary instruction 404 and the secondary instruction 406 as illustrated. However, the first booklet 200 may comprise one or more instructions that are not present in the second booklet 300 and vice versa.

The first primary page 204 comprises instructions 404 for handling a primary emergency situation. The first secondary page 206 comprises instructions 406 for handling a secondary emergency situation. The second primary page 304 comprises the instructions 404 for handling the primary emergency situation. The second secondary page 306 comprises the instructions 406 for handling the secondary emergency situation.

The first booklet 200 and/or the second booklet 300 may comprise a plurality of identifiers, such as QR-codes, bar-codes, RFID-tags and/or NFC-tags. The plurality of identifiers may be unique identifiers. The identifiers are configured to be electronically read by the portable electronic device 10. The identifiers may be indicative of the respective booklet, such as a respective booklet ID, the respective page, such as a respective page ID, and/or a respective emergency situation, such as a situation ID. The pages of each booklet may be provided with unique identifiers by providing individual production files for each booklet for printing.

The first booklet 200 comprises a plurality of first identifiers. The first identifiers are configured to be electronically read by the portable electronic device 10. The plurality of first identifiers includes a first primary identifier 214 provided on the first primary page 204 and a first secondary identifier 216 provided on the first secondary page 206. The plurality of first identifiers may include a first main identifier 212 provided on the first main page 202.

The second booklet 300 comprises a plurality of second identifiers. The second identifiers are configured to be electronically read by the portable electronic device 10. The plurality of second identifiers includes a second primary identifier 314 provided on the second primary page 304 and a second secondary identifier 316 provided on the second secondary page 306. The plurality of second identifiers may include a second main identifier 312 provided on the second main page 302.

The identifiers, such as the plurality of first identifiers and/or the plurality of second identifiers may be optical detectable identification elements, such as QR-codes or bar-codes. Alternatively or additionally, the identifiers, such as the plurality of first identifiers and/or the plurality of second identifiers may be electromagnetic field identification elements, such as RFID-tags or NFC-tags.

The identifiers are configured to prompt an identification signal at the portable electronic device 10. For example, the first primary identifier 214 is configured to prompt a first primary identification signal 224 at the portable electronic device 10, and the first secondary identifier 216 is configured to prompt a first secondary identification signal 226 at the portable electronic device 10. The first main identifier 212 may be configured to prompt a first main identification signal 222 at the portable electronic device 10. Alternatively or additionally, the second primary identifier 314 is configured to prompt a second primary identification signal 324 at the portable electronic device 10, and the second secondary identifier 316 is configured to prompt a second secondary identification signal 326 at the portable electronic device 10. The second main identifier 312 may be configured to prompt a second main identification signal 322 at the portable electronic device 10.

The identification signal(s), such as the first primary identification signal 224, the first secondary identification signal 226, the first main identification signal 222, the second primary identification signal 324, the second secondary identification signal 326, and/or the second main identification signal 322, could be complete URI and instruction to open a browser.

The identification signal(s), such as the first primary identification signal 224, the first secondary identification signal 226, the first main identification signal 222, the second primary identification signal 324, the second secondary identification signal 326, and/or the second main identification signal 322, may comprise a plurality of identifier components, such as a server address, a first parameter, and/or a second parameter.

The first primary identification signal 224 may be distinct from the first secondary identification signal 226, the first main identification signal 222, the second primary identification signal 324, the second secondary identification signal 326 and/or the second main identification signal 322. The first secondary identification signal 226 may be distinct from the first main identification signal 222, the second primary identification signal 324, the second secondary identification signal 326 and/or the second main identification signal 322. The first main identification signal 222 may be distinct from the second primary identification signal 324, the second secondary identification signal 326 and/or the second main identification signal 322. The second primary identification signal 324 may be distinct from the second secondary identification signal 326 and/or the second main identification signal 322. The second secondary identification signal 326 may be distinct from the second main identification signal 322.

One or more of the identification signals, such as the first primary identification signal 224, the first secondary identification signal 226, the first main identification signal 222, the second primary identification signal 324, the second secondary identification signal 326, and/or the second main identification signal 322, may comprise server information of the online server 100, e.g. configured to prompt the portable electronic device 10 to contact the online server 100. For example, the identification signals, or one or more of the identification signals may comprise a web-address to the online server 100.

One or more of the identification signals may comprise server information of the online server 100, e.g. configured to prompt the portable electronic device 10 to contact the online server and parse to the online server the respective identification parameter.

The first primary identification signal 224 may comprise server information of the online server 100 configured to prompt the portable electronic device 10 to contact the online server 100 and parse the first primary identification parameter 234 to the online server 100.

The first secondary identification signal 226 may comprise server information of the online server 100 configured to prompt the portable electronic device 10 to contact the online server 100 and parse the first secondary identification parameter 236 to the online server 100.

The first main identification signal 222 may comprise server information of the online server 100 configured to prompt the portable electronic device 10 to contact the online server 100 and parse the first main identification parameter 232 to the online server 100.

The second primary identification signal 324 may comprise server information of the online server 100 configured to prompt the portable electronic device 10 to contact the online server 100 and parse the second primary identification parameter 334 to the online server 100.

The second secondary identification signal 326 may comprise server information of the online server 100 configured to prompt the portable electronic device 10 to contact the online server 100 and parse the second secondary identification parameter 336 to the online server 100.

The second main identification signal 322 may comprise server information of the online server 100 configured to prompt the portable electronic device 10 to contact the online server 100 and parse the second main identification parameter 332 to the online server 100.

The first identification parameters, such as the first primary identification parameter 234, the first secondary identification parameter 236, and/or the first main identification parameter 232 may comprise a first booklet ID, e.g. indicative of the first booklet 200. The second identification parameters, such as the second primary identification parameter 334, the second secondary identification parameter 336, and/or the second main identification parameter 332 may comprise a second booklet ID, e.g. indicative of the second booklet 300. Thereby, the online server 100 may be notified from which booklet the identifier was registered.

The online server 100 may store information about locations of booklets of the system 2, such as location of the first booklet 200 and/or the second booklet 300. The location may be geographical coordinates, a defined geographical area, and/or an address. The location of the booklet may be paired with the respective booklet ID at the online server 100, such as in the server database 102 of the server 100. For example, the online server 100 may store information about the location of the first booklet 200 paired with the first booklet ID and/or the online server 100 may store information about the location of the second booklet 300 paired with the second booklet ID. Thereby, receiving an identification parameter comprising a booklet ID, the online server 100 may be able to determine the location of the registered identifier, e.g. based on the booklet ID.

By using a main identifier, such as the first main identifier or the second main identifier, the user may register the location of respective booklet, e.g. the respective booklet ID, on the server. For example, the first main identification parameter 232 may cause the online server 100 to request 104 from the portable electronic device 10 an input indicative of the location of the first booklet 200. The second main identification parameter 332 may cause the online server 100 to request 104 from the portable electronic device 10 an input indicative of the location of the second booklet 300.

Alternatively or additionally, the online server 100 may be configured to register the location of the respective booklet the first time identification parameters of a booklet, which is not yet registered, is parsed to the online server. For example, the first primary identification parameter 234 and/or the first secondary identification parameter 236 may, in accordance with the first booklet 200 not being registered with the online server, cause the online server 100 to request 104 from the portable electronic device 10 an input indicative of the location of the first booklet 200. The second primary identification parameter 334 and/or the second secondary identification parameter 336 may, in accordance with the second booklet 300 not being registered with the online server, cause the online server 100 to request 104 from the portable electronic device 10 an input indicative of the location of the second booklet 300.

The first main identification parameter 232 may, e.g. in accordance with the first booklet 200 already being registered, cause the online server 100 to provide at the portable electronic device 10 a first profile page, e.g. comprising a list of registered emergency situations using the first booklet 200. Additionally or alternatively, the second main identification parameter 332 may, e.g. in accordance with the second booklet 300 already being registered, cause the online server 100 to provide at the portable electronic device 10 a second profile page, e.g. comprising a list of registered emergency situations using the second booklet 300.

The online server 100 is configured to receive identification parameters from the portable electronic device 10. The identification parameter may include one or more of a first primary identification parameter 234 of the first primary identification signal 224, a first secondary identification parameter 236 of the first secondary identification signal 226, a second primary identification parameter 334 of the second primary identification signal 324, a second secondary identification parameter 336 of the second secondary identification signal 326.

The online server is further configured to in accordance with receiving the first primary identification parameter 234, registering an event in a server database 102 of an occurrence of the primary emergency situation 404 at a first location based on the first primary identification parameter 234, wherein the first location corresponds to a location of the first booklet 200.

The online server is further configured to in accordance with receiving the first secondary identification parameter 236, registering an event in the server database 102 of an occurrence of the secondary emergency situation 406 at the first location based on the first secondary identification parameter 236.

The online server may further be configured to in accordance with receiving the second primary identification parameter 334, registering an event in the server database 102 of an occurrence of the primary emergency situation 404 at a second location based on the second primary identification parameter 334, wherein the second location corresponds to a location of the second booklet 300.

The online server may further be configured to in accordance with receiving the second secondary identification parameter 336, registering an event in the server database 102 of an occurrence of the secondary emergency situation 406 at the second location based on the second secondary identification parameter 336.

The online server may store information about emergency situations paired with respective identification parameters. For example, the online server may store information about the primary emergency situation paired with primary identification parameters, e.g. including the first primary identification parameter 234 and/or the second primary identification parameter 334. Alternatively or additionally, the online server may store information about the secondary emergency situation paired with secondary identification parameters, e.g. including the first secondary identification parameter 236 and/or the second secondary identification parameter. Thereby, the online server 100 may determine the subject of the information on the page of which the identifier was registered.

For example, the primary identification parameters, such as the first primary identification parameter 234 and/or the second primary identification parameter 334 may comprise a primary situation ID indicative of the primary emergency situation. Alternatively or additionally, the secondary identification parameters, such as the first secondary identification parameter 236 and/or the second secondary identification parameter 336 may comprise a secondary situation ID indicative of the secondary emergency situation. The online server 10 may be configured to determine the respective emergency situation based on the situation ID of the received identification parameter.

Alternatively or additionally, the first primary identification parameter 234 may comprise a first primary page ID indicative of the first primary page 204, the first secondary identification parameter 236 may comprise a first secondary page ID indicative of the first secondary page 206, the second primary identification parameter 334 may comprise a second primary page ID indicative of the second primary page 304, and/or the second secondary identification parameter 336 may comprise a second secondary page ID indicative of the second secondary page 306. The online server 10 may be configured to determine the respective emergency situation based on the page ID and the booklet ID of the received identification parameter.

The online server 100 may be further configured to, following registering an event in the server database, providing via the portable electronic device 10 an input option for supplementing the registered event with additional information, such as, photo(s), free text, description, comments, etc.

The online server 100 may be further configured to, following registering an event in the server database, providing via the portable electronic device 10 a summary of the registered event and optionally a user input element for verifying or denying correctness of the summary. The online server 100 may be further configured to: upon receipt of a signal from the portable electronic device 10 indicative of the user verifying correctness of the summary, storing the registered event in the server database; and upon receipt of a signal from the portable electronic device 10 indicative of the user denying correctness of the summary, deleting the registered event from the server database.

Thus, with the above described system 2, a first responder responds to a primary emergency situation. In doing so, the first responder brings the first booklet 200. In handling the situation, the first responder looks up the first primary page 204 comprising instructions for handling a primary emergency situation 404. After having dealt with the primary emergency situation 404, the first responder retrieves his portable electronic device 10, activates the camera 12 and scans the first primary identifier 214 being provided on the first primary page 204.

The first primary identifier 214 prompts the first primary identification signal 224 at the portable electronic device 10, causing the portable electronic device 10 to open a webpage for the online server 100. The online server 100, e.g. by the opening of the webpage by the portable electronic device 10, receives first primary identification parameter 234 of the first primary identification signal 224, which comprise information indicative of the primary emergency situation, e.g. nosebleed, broken arm, etc. as well as the registered location of the first booklet 200.

The online server 100 thereby registers an event in the server database 102 of an occurrence of the primary emergency situation at the first location corresponding to the location of the first booklet 200. The necessary information is thereby stored in the server database 102 in a fast and convenient way.

The opened web page may further provide an optional possibility for the first responder to add pictures and/or supplemental text, which may be submitted by pressing a submit button.

The invention has been described with reference to a preferred embodiment. However, the scope of the invention is not limited to the illustrated embodiment, and alterations and modifications can be carried out without deviating from the scope of the invention.

Throughout the description, the use of the terms "first", "second", "third", "fourth", "primary", "secondary", "tertiary" etc. does not imply any particular order or importance but are included to identify individual elements. Furthermore, the labelling of a "first" element does not imply the presence of a "second" element and vice versa.

LIST OF REFERENCES 2 system
10 portable electronic device
12 camera
14 processing unit
16 memory
100 online server
102 server database
104 request
200 first booklet
202 first main page
204 first primary page
206 first secondary page
212 first main identifier
214 first primary identifier
216 first secondary identifier
222 first main identification signal
224 first primary identification signal
226 first secondary identification signal
232 first main identification parameter
234 first primary identification parameter
236 first secondary identification parameter
300 second booklet
302 second main page
304 second primary page
306 second secondary page
312 second main identifier
314 second primary identifier
316 second secondary identifier
322 second main identification signal
324 second primary identification signal 326 second secondary identification signal
332 second main identification parameter
334 second primary identification parameter
336 second secondary identification parameter
404 instructions for handling a primary emergency situation
406 instructions for handling a secondary emergency situation

The invention claimed is:

1. System for registering emergency situations, the system comprises:
a portable electronic device;
an online server configured to communicate with the portable electronic device over a network; and
a first booklet comprising a plurality of first pages including a first primary page and a first secondary page, the first primary page comprising instructions for handling a primary emergency situation, the first secondary page comprising instructions for handling a secondary emergency situation, the first booklet comprises a plurality of first identifiers configured to be electronically read by the portable electronic device, the plurality of first identifiers including a first primary identifier provided on the first primary page and a first secondary identifier provided on the first secondary page, the first primary identifier being configured to prompt a first primary identification signal at the portable electronic device and the first secondary identifier being configured to prompt a first secondary identification signal at the portable electronic device, the first primary identification signal being distinct from the first secondary identification signal, the portable electronic device being configured to:
scan the first primary identifier, in response to the scan of the first primary identifier, generate the first primary identification signal, and in response to the first primary identification signal, access a first webpage associated with the online server;
scan the first secondary identifier and, in response to the scan of the first secondary identifier, generate the first secondary identification signal, and in response to the first secondary identification, access a second webpage associated with the online server;
the online server being configured to receive identification parameters including, in response to the access of the first webpage, a first primary identification parameter of the first primary identification signal, and in response to the access of the second webpage, a first secondary identification parameter of the first secondary identification signal from the portable electronic device, the online server is further configured to:
in accordance with receiving the first primary identification parameter, determining, based on information stored in a server database, that the first primary identification parameter is paired with the primary emergency situation at a first location and, in response to the determination, registering an event in the server database of an occurrence of the primary emergency situation at the first location, wherein the first location corresponds to a location of the first booklet, and
in accordance with receiving the first secondary identification parameter, determining, based on the information stored in the server database, that the first secondary identification parameter is paired with the secondary emergency situation at the first location and, in response to the determination, registering an event in the server database of an occurrence of the secondary emergency situation at the first location.

2. The system of claim 1, wherein the first primary identification signal and/or the first secondary identification signal comprises server information of the online server configured to prompt the portable electronic device to contact the online server.

3. The system of any of claim 1, wherein the first primary identification signal comprises server information of the online server configured to prompt the portable electronic device to contact the online server and parse the first primary identification parameter to the online server and/or the first secondary identification signal comprises server information of the online server configured to prompt the portable electronic device to contact the online server and parse the first secondary identification parameter to the online server.

4. The system of any of claim 1, wherein the plurality of first identifiers are optical detectable identification elements, such as QR-codes or bar-codes.

5. The system of claim 1, wherein the plurality of first identifiers are electromagnet field identification elements, such as RFID-tags or NFC-tags.

6. The system of claim 1, wherein the portable electronic device is a smart phone or a tablet.

7. The system of claim 1, wherein the first primary identification parameter comprises a first booklet ID indicative of the first booklet, and wherein the first secondary identification parameter comprises the first booklet ID.

8. The system of claim 7, wherein the plurality of first identifiers includes a first main identifier provided on a first main page, the first main identifier being configured to prompt a first main identification signal at the portable electronic device, wherein the first main identification signal comprises a first main identification parameter comprising the first booklet ID indicative of the first booklet, and wherein the first main identification signal comprises server information of the online server configured to prompt the portable electronic device to contact the online server and parse the first main identification parameter to the online server, wherein the first main identification parameter causes the online server to request from the portable electronic device an input indicative of the location of the first booklet.

9. The system of claim 7, wherein the online server stores information about the location of the first booklet paired with the first booklet ID.

10. The system of claim 1, wherein the online server stores information about the primary emergency situation paired with primary identification parameters including the first primary identification parameter and the secondary emergency situation paired with secondary identification parameters including the first secondary identification parameter.

11. The system of claim 1 comprising a second booklet comprising a plurality of second pages including a second primary page and a second secondary page, the second primary page comprising instructions for handling the primary emergency situation, the second secondary page comprising instructions for handling the secondary emergency situation, the second booklet comprises a plurality of second identifiers configured to be electronically read by the portable electronic device, the plurality of second identifiers including a second primary identifier provided on the second primary page and a second secondary identifier provided on the second secondary page, the second primary identifier being configured to prompt a second primary identification signal at the portable electronic device and the second secondary identifier being configured to prompt a second secondary identification signal at the portable electronic device, the second primary identification signal being distinct from the second secondary identification signal.

12. The system according to claim 11, wherein the online server is further configured to:
- in accordance with receiving a second primary identification parameter of the second primary identification signal, registering an event in the server database of an occurrence of the primary emergency situation at a second location based on the second primary identification parameter, wherein the second location corresponds to a location of the second booklet, and
- in accordance with receiving a second secondary identification parameter of the second secondary identification signal, registering an event in the server database of an occurrence of the secondary emergency situation at the second location based on the second secondary identification parameter.

13. The system according to claim 1, wherein the online server is further configured to, following registering an event in the server database, providing via the portable electronic device an input option for supplementing the registered event with additional information.

14. The system according to claim 1, wherein the online server is further configured to, following registering an event in the server database, providing via the portable electronic device a summary of the registered event and a user input element for verifying or denying correctness of the summary, and wherein the online server is configured to:
- upon receipt of a signal from the portable electronic device indicative of the user verifying correctness of the summary, storing the registered event in the server database, and
- upon receipt of a signal from the portable electronic device indicative of the user denying correctness of the summary, deleting the registered event from the server database.

* * * * *